United States Patent [19]

Smith

[11] Patent Number: 5,480,637
[45] Date of Patent: Jan. 2, 1996

[54] ALKYLMETHYLSILOXANE CONTAINING GELS

[75] Inventor: Janet M. Smith, Baycity, Mich.

[73] Assignee: Dow Corning Corporation, Midland, Mich.

[21] Appl. No.: 324,045

[22] Filed: Oct. 17, 1994

[51] Int. Cl.$^6$ ............... A61K 7/32; A61K 7/38; A61K 31/765
[52] U.S. Cl. ............ 424/78.02; 424/65; 424/68; 424/401; 514/944
[58] Field of Search ............ 424/65, 68, 78.02, 424/401; 514/944

[56] References Cited

U.S. PATENT DOCUMENTS

| | | | |
|---|---|---|---|
| 3,641,239 | 2/1972 | Mohrlok | 424/64 |
| 5,225,188 | 7/1993 | Abrutyn | 424/66 |
| 5,284,649 | 2/1994 | Juneja | 424/67 |
| 5,320,828 | 6/1994 | Conway | 424/47 |

FOREIGN PATENT DOCUMENTS 9323008  11/1993  WIPO.

Primary Examiner—Jyothsna Venkat
Attorney, Agent, or Firm—James L. DeCesare

[57] ABSTRACT

A gel suitable for use in personal care applications is provided. The improved gel contains a gelator; an oil; and an alkylmethylsiloxane polymer or copolymer for strengthening the gel, and increasing its firmness and rigidity. The gelator is 12-hydroxystearic acid or metal salts of 12-hydroxystearic acid. A suitable oil is a non-volatile siloxane mixed with a volatile methyl siloxane having a boiling point less than two hundred-fifty degrees Centigrade and a viscosity in the range of 0.65 to 5.0 centistokes (mm$^2$/s).

1 Claim, No Drawings

ALKYLMETHYLSILOXANE CONTAINING GELS

BACKGROUND OF THE INVENTION

This invention is directed to a clear firm gel suitable for use in various personal care applications. The improved gel includes a gelator; an alkylmethylsiloxane polymer or copolymer for improving the clarity of the gel, and for strengthening the gel, and increasing its firmness and rigidity; and an oil.

Recent trends in consumer buying has shifted in emphasis to a demand for clear products. These products range from fuels for automotive vehicles, to household and personal care products including dish washing and laundry detergents, as well as skin and hair care products in the form of lotions, solutions, and gels. One is apt to find on store shelves consumer oriented products such as clear shampoos, clear sunscreens, clear bath oils, clear deodorants, clear antiperspirants, and clear dentifrices. Since consumers tend to equate clarity with environmental friendliness and purity, the demand for clear products is likely to continue.

It is difficult to produce a clear product. In the case of stick type products, it is also difficult to produce a solid product with the appropriate rigidity. Not all basic ingredients necessary to formulate clear products lend themselves to clarity, or to firmness for that matter, particularly when they are combined with all of the other ingredients required for a successful formulated product. This is especially true in formulations found in the personal care arena.

Thus, the problem sought to be solved by the present invention is the production of a gel product, suitable for use as a base ingredient in personal care applications. This problem is solved according to the invention, by combining certain basic components into a formulation.

The benefits and advantages derived from the invention are that a solid product which is effective for use as a component in personal care products can effectively be produced which will meet consumer demands for clarity and rigidity in the marketplace.

SUMMARY OF THE INVENTION

The invention relates to a clear, firm, rigid, gel containing 0.1 to 10 percent by weight of an alkylmethylsiloxane polymer or copolymer; 0.1 to 10 percent by weight of a gelator which can be 12-hydroxystearic acid or a metal salt of 12-hydroxystearic acid; and 80 to 99.8 percent by weight of an oil. The oil can be an organic oil, a volatile or non-volatile siloxane, or mixtures thereof. For purposes of the invention, a volatile siloxane is considered a compound having a boiling point less than two hundred-fifty degrees Centigrade and a viscosity of 0.65 to about 5.0 centistoke ($mm^2/s$).

While not being bound by any particular theory, it is believed that the increase of strength of the gels of the invention, as well as their increase in clarity, is due to an increased interaction between the 12-hydroxystearic acid gelator and the alkylmethylsiloxane. Because the gelator is amide-free, this interaction is unhindered by the presence of any amide-type co-gelator, such as those taught in US 0530671/EP 0 531 337 which was published Nov. 25, 1993 as WO 93/23008.

Thus, according to the present invention, the alkylmethylsiloxane functions to increase the intermolecular forces between the oil and the 12-hydroxystearic acid gelator, in order to control the size and the number of the microfibers which are formed, and this in turn improves the strength and the clarity of the gels.

Furthermore, the alkylmethylsiloxane of this invention functions to increase the solubility of the amide-free 12-hydroxystearic acid gelator in the oil. As a result, a large number of nucleation sites are formed during crystallization, and these sites have the potential of producing a large number of microfibers. A high fiber density is thereby produced, and the high fiber density causes the gels to become stronger in exhibiting a higher modulus. Since the microfibers are of a very small size, they cause less light scattering and the gels are clear.

According to this invention, clarity is defined in terms of Nephelometric Turbidity Units (NTU). Readings of less than 400 NTU are considered clear; readings greater than 400 NTU are considered translucent; and readings under 100 NTU are considered water clear.

These and other features, objects, and advantages, of the present invention will become more apparent from a consideration of the following detailed description thereof.

DETAILED DESCRIPTION OF THE INVENTION

Gels according to the invention are clear, firm, and rigid, and contain 0.1 to 10 percent by weight of an alkylmethylsiloxane polymer or copolymer; 0.1 to 10 percent by weight of a gelator which can be 12-hydroxystearic acid or a metal salt of 12-hydroxystearic acid; and 80 to 99.8 percent by weight of an organic oil, a volatile siloxane or non-volatile siloxane, or mixtures thereof.

When it is desired to formulate a personal care product such as an antiperspirant, the composition of the gel can contain in addition an antiperspirant active. In those instances, the gel should contain 0.1 to 10 percent by weight of the alkylmethylsiloxane polymer or copolymer; 0.1 to 10 percent by weight of the gelator; 55 to 89.8 percent by weight of the oil component; and 10 to 25 percent by weight of an appropriate antiperspirant active.

Suitable antiperspirant actives are astringent salt compounds typically inorganic or organic salt forms of aluminum or zirconium, including mixtures thereof. Representative compounds are aluminum chloride, aluminum chlorohydrate, aluminum dichlorohydrate, aluminum chlorohydrex, aluminum sesquichlorohydrate, aluminum-zirconium chlorohydrate, aluminum-zirconium trichlorohydrate, aluminum-zirconium pentachlorohydrate, aluminum-zirconium octachlorohydrate, aluminum-zirconium chlorohydroglycine, aluminum-zirconium tetrachlorohydrexglycine, zirconium chlorohydrate, and zirconium hydroxychloride.

One preferred type of astringent antiperspirant salt is an encapsulated aluminum chlorohydrate, described for example in U.S. Pat. No. 5,320,828. In formulating clear products, the refractive index of the astringent antiperspirant salt compound should match the refractive index of the siloxane fluids.

The alkylmethylsiloxane of the invention is a polymer or copolymer having one of the following formulas:

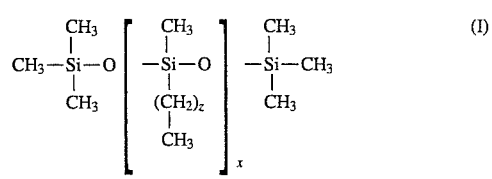

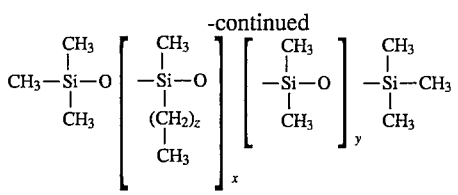

(II)

in which x has a value of 1–50; y has a value of 1–100; and z has a value of 10–40.

It is contemplated that one or both of the terminal methyl radicals in Formulas (I) or (II) above, could be replaced with the group —(CH$_2$)$_z$CH$_3$. Representative of such alkylmethylsiloxane structures are shown below.

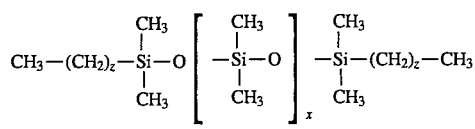

(III)

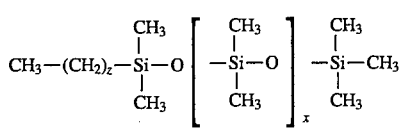

(IV)

These alkylmethylsiloxanes can be produced by the reaction of a linear siloxane having Si—H functionality in the chain with a slight stoichiometric excess of an alkene CH$_2$=CHR in the presence of a platinum on carbon catalyst. Alkylmethylsiloxanes can also be produced by the direct co-hydrolysis of methylhydrogen dichlorosilane and trimethylchlorosilane. The reaction product is contacted with a slight stoichiometric excess of an alkene CH$_2$=CHR in the presence of a platinum on carbon catalyst.

Batch production of alkylmethylsiloxanes is conducted by adding the reaction product to a non-agitated suspension of the catalyst in the alkene at about sixty degrees Centigrade. Continuous production of alkylmethylsiloxanes is conducted by pumping a preheated solution of a five percent stoichiometric excess of an alkene CH$_2$=CHR and the reaction product through a packed column containing platinum on carbon catalyst chips. The column requires provision for the removal of heat because of the exothermic nature of the reaction.

Preferably, the alkylmethylsiloxane contain at most about five parts per million of residual alkene and about 99.95 percent alkylmethylsiloxane product. No measurable residual amount of platinum can be detected. These products are colorless, odorless, clear and stable materials.

The amide-free gelator is 12-hydroxystearic acid or a metal salt of 12-hydroxystearic acid. The acid has the formula CH$_3$(CH$_2$)$_5$CH(OH)(CH$_2$)$_{10}$COOH. Metal salts of 12-hydroxystearic acid can also be employed as gelator. Such salts have the formula [C$_6$H$_{13}$—CH(OH)—(CH$_2$)$_{10}$—COO]$_n$M in which M indicates a metal such as Li+, Na+, K+, Rb+, Cs+, Mg(2+), Ca(2+), Sr(2+), Ba(2+), Mn(2+), Ni(2+), Cu(2+), Zn(2+), Cd(2+), Hg(2+), Co(2+), and Pb(2+); and the value of n is one for monovalent cations and two for divalent cations. An example of metal salts suitable for use according to the invention are calcium 12-hydroxystearate and lithium 12-hydroxystearate. These metal salts can be prepared by the direct neutralization of 12-hydroxystearic acid with a metal base such as sodium hydroxide or potassium hydroxide. The metal salts can also be prepared by a metathesis reaction of a simple metal salt such as sodium 12-hydroxystearate with a metal sulfate salt or a metal chloride salt such as zinc chloride or copper sulfate.

The oil is an organic emollient oil such as mineral oil, peanut oil, sesame oil, avocado oil, coconut oil, cocoa butter, almond oil, safflower oil, corn oil, cotton seed oil, castor oil, olive oil, jojoba oil, paraffin oil, cod liver oil, palm oil, soybean oil, wheat germ oil, linseed oil, and sunflower seed oil; fatty acid esters such as isopropyl myristate, isopropyl palmitate, isopropyl stearate, bury stearate, cetyl stearate, diisopropyl adipate, isodecyl oleate, diisopropyl sebacate, and lauryl lactate; fatty acids such as lauric, myristic, palmitic, stearic, oleic, linoleic, and behenic, acid; fatty alcohols such as lauryl, myristyl, cetyl, stearyl, isostearyl, oleyl, ricinoleyl, erucyl, and 2-octyl dodecanol, alcohol; lanolin and its derivatives such as lanolin, lanolin oil, lanolin wax, lanolin alcohols, lanolin fatty acids, isopropyl lanolate, ethoxylated lanolin, and acetylated lanolin alcohols such as ACETULAN®, a trademark and product of Amerchol Corporation, Edison, N.J.; and hydrocarbons such as petrolatum and squalane. A particularly preferred organic emollient oil is a C12 to C15 alcohol benzoate sold under the tradename FINSOLV TN by Finerex Inc. of Elmwood Park, N.J.

Organic oils which are sunscreen agent can be employed provided they are used in amounts which are within the restricted limits or less as established by the United States Government Food & Drug Administration (FDA). Representative sunscreen agents or mixtures of such agents which may be used in the preparation of the compositions of the present invention include 4-aminobenzoic acid; homomethyl salicylate; 2-hydroxy-4-methoxy benzophenone; 2-phenylbenzimidazol-5-sulfonic acid; 4dimethylamino benzoic acid 2-ethylhexyl ester; 4-methoxy cinnamic acid isoamyl ester; 4-methoxy cinnamic acid 2-ethylhexyl ester (CTFA Octyl Methoxycinnamate); 3-(4'-methyl) benzylidine-bornane-2-one; 1-(4'-isopropylphenyl)-3-phenyl-l-propane-l, 3-dione; 1-(4'-t-butylphenyl)-3-(4-methoxyphenyl)-propane-1,3-dione; and 2-ethylhexyl 2-hydroxybenzoate (CTFA Octyl Salicylate).

Most preferred of the sunscreen agents are Octyl Salicylate and Octyl Methoxycinnamate. Octyl Salicylate is sold under the tradenames DERMOBLOCK OS by Alzo Inc. of Matawan, N.J.; ESCALOL 587 by ISP Van Dyk of Belleville, N.J.; NEOTAN L by Fabriquimica SRL of San Martin, Argentina; and UNIVUL 0-18 by BASF Corporation of Parsippany, N.J. Octyl methoxycinnamate is sold under the tradenames ESCALOL 557 by ISP Van Dyk of Belleville, N.J.; and PARSOL MCX by Givaudan-Route Corporation of Clifton, N.J.

Organic fragrance oils can also be employed including natural products such as ambergris, benzoin, civet, clove, leaf oil jasmine mate', mimosa, musk, myrrh, orris, sandalwood oil and vetivert oil; aroma chemicals such as amyl salicylate, amyl cinnamic aldehyde, benzyl acetate, citronellol, coumarin, geraniol, isobornyl acetate, ambrette, and terpinyl acetate; and the various classic family perfume oils such as the floral bouquet family, the oriental family, the chypre family, the woody family, the citrus family, the canoe family, the leather family, the spice family, and the herbal family.

As previously noted, the oil can include a non-volatile siloxane, a volatile siloxane, or mixtures thereof. The non-volatile siloxane is an organic polysiloxane having a viscosity in excess of five and preferably in the range of 100 to about 10,000 Centistokes (mm$^2$/s). A mixture of polysiloxanes having relatively higher and relatively lower viscosities may be employed. Such polysiloxanes have the repeating unit

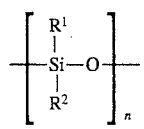

in which n is an integer having a value greater than one; and $R^1$ and $R^2$ are typically short-chain alkyl radicals such as methyl, or a phenyl group. Illustrative non-volatile siloxanes are polydimethylsiloxane, polydiethylsiloxane, polymethylethylsiloxane, polymethylphenylsiloxane, and polydiphenylsiloxane.

Most preferably, the non-volatile siloxane is an aromatic organic group containing siloxane having one of the following formulas:

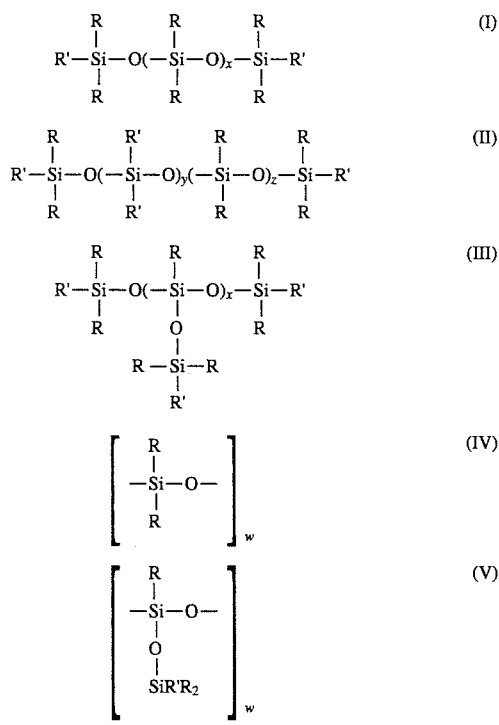

In formulas (I) to (V), R is R', an aromatic organic radical such as a phenyl radical, or an aralkyl radical such as 2-phenylethyl, 2-phenylpropyl, and 2-phenylbutyl; R' is an alkyl radical having from one to seven carbon atoms; x is an integer having a value of zero to one thousand; w is an integer having a value of three to six; y and z are integers the sum of which is between two and one thousand. For purposes of this invention, R' is most preferably methyl, and R is methyl, phenyl, or 2-phenylpropyl; and x has a value of 1 to 1,000.

The aromatic organic group containing siloxane used is most preferably phenyl substituted, has a viscosity of less than fifty centistokes (mm²/s), a molecular weight of less than 1,000, a refractive index of 1.48 to 1.53, and at least two phenyl groups as substituents on silicon atoms, with the remaining substituents on silicon atoms being methyl groups.

Below are some representative aromatic organic group containing siloxanes, including phenyl substituted and 2-phenylpropyl functional fluids, which can be used according to the invention. All fluid viscosities are measured at 25° Centigrade. Thus, representative aromatic organic group containing siloxanes are (i) a methylphenyl polysiloxane fluid having a viscosity of twenty Centistokes (MM²s); (ii) a tetramethyltetraphenyl trisiloxane fluid (TMTPTS) having a viscosity of thirty-seven Centistokes (mm²/s); (iii) a diphenyltetramethyl disiloxane fluid having a viscosity of 3.5 Centistokes (mm²/s); (iv) a phenylmethyldimethyl cyclosiloxane fluid having a viscosity of forty-five Centistokes (mm²/s); (v) a methylstyrene-methicone fluid of the formula $(CH_3)_3SiO(CH_3RSiO)_{7.06}Si(CH_3)_3$ in which R is $—CH_2CH(CH_3)C_6H_5$ and having a viscosity of one hundred seventy Centistokes (mm²/s); (vi) a methylstyrene-methicone fluid of the formula $(CH_3)_3SiO(CH_3RSiO)_3Si(CH_3)_3$ in which R is $—CH_2CH(CH_3)C_6H_5$ and having a viscosity of fifty-two Centistokes (mm²/s); and (vii) a copolymeric methylstyrene-methicone fluid of the formula $(CH_3)_3SiO[(CH_3)_2SiO]_4(CH_3RSiO)_{4.5}Si(CH_3)_3$ in which R is $—CH_2CH(CH_3)C_6H_5$ and having a viscosity of forty-eight Centistokes (mm²/s). Chemically, fluids (v) and (vi) are poly(2-phenylpropylmethylsiloxane), and fluid (vii) is poly(2-phenylpropylmethylsiloxane-dimethylsiloxane).

These aromatic organic group containing siloxane fluids can be used alone, or as blends by combining two or more of the fluids as blended mixtures. In addition, one or more of the aromatic organic group containing siloxane fluids can be combined with other types of siloxane fluids such as a volatile siloxane. Where two or more fluids are blended, at least one of the fluids should have at least two phenyl groups or two aralkyl groups as substituents on silicon atoms, with the remaining substituents on silicon atoms being methyl groups.

Methods of making aromatic organic group containing siloxane fluids are known in the art. Representative methods can be found in U.S. Pat. Nos. 3,088,964, 3,186,944, 3,221,040, and 3,839,384. Phenylpropylalkyl cyclosiloxanes can be made according to a method described in an article entitled "*Addition of Silicon Hydrides to Olefinic Double Bonds. IV. The Addition to Styrene and alpha-Methylstyrene*", by John L. Speier and John W. Ryan, Journal of Organic Chemistry, Volume 24, Pages 2052–2053, Dec. 1959. Generally such methods involve either (i) hydrolyzing phenylpropylmethyl silanes, or (ii) reacting alpha-methylstyrene with an organosiloxane containing ≡SiH groups in the molecule.

The volatile siloxane according to the invention is a low viscosity fluid which corresponds to the average unit formula $(CH_3)_aSiO_{(4-a)/2}$ in which a has an average value of two or three. The fluid contains siloxane units Joined by Si—O—Si bonds. Representative units present in the fluid molecule are the monofunctional unit $(CH_3)_3SiO_{1/2}$ and the difunctional unit $(CH_3)_2SiO_{2/2}$. The presence of the trifunctional unit $CH_3SiO_{3/2}$ will generally result in the formation of branched cyclic volatile methyl siloxanes. The presence of the tetrafunctional unit $SiO_{4/2}$ will generally result in the formation of branched linear volatile methyl siloxanes. These units are present in molar amounts such that there is provided an average of from about two to three methyl groups per silicon atom in the fluid.

Representative volatile methyl siloxanes are cyclopolysiloxanes of the formula $[(CH_3)_2SiO]_x$, and linear siloxanes of the formula $(CH_3)_3SiO[(CH_3)_2SiO]_ySi(CH_3)_3$, in which x has a value of three to six, and y has a value of zero to five. These volatile methyl siloxanes have boiling points generally less than about two hundred-fifty degrees Centigrade, and a viscosity typically in the range of 0.65 to about 5.0 centistokes (mm²/s).

Some structures which are representative of volatile methyl siloxanes are shown below:

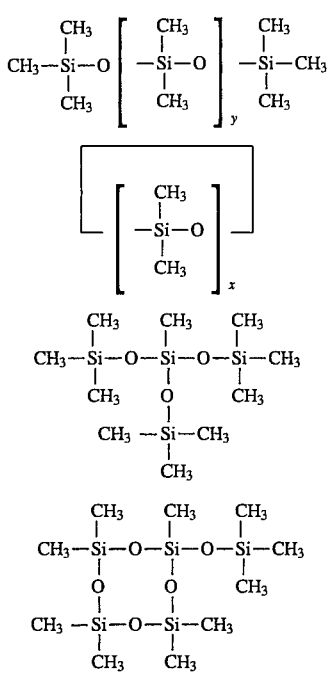

Structure I represents a linear volatile methyl siloxane. Structure II represents a cyclic volatile methyl siloxane. Structure III represents a branched linear volatile methyl siloxane. Structure IV represents a branched cyclic volatile methyl siloxane. The values of x and y in Structures I and II are the same as noted previously. The cyclic volatile methyl siloxane (II) has been assigned the International Nomenclature Cosmetic Ingredient (INCI) name "CYCLOMETHICONE" by The Cosmetics, Toiletries and Fragrance Association, Inc. (CTFA), Washington, D.C.

The cyclic and linear methyl siloxanes are clear fluids, and are essentially odorless, nontoxic, non-greasy and non-stinging. Cosmetically, the fluids are nonirritating to skin, spread easily when applied to the skin, and once applied, evaporate leaving behind no residue.

The volatile methyl siloxanes leave substantially no residue after thirty minutes at room temperature when one gram of the fluid is placed at the center of No. 1 circular filter paper which has a diameter of 185 millimeters and which is supported at its perimeter in open room atmosphere. Some representative linear volatile methyl siloxanes are hexamethyldisiloxane which has a boiling point of 100 degrees Centigrade and the formula $Me_3SiOSiMe_3$; octamethyltrisiloxane which has a boiling point of 152 degrees Centigrade and the formula $Me_3SiOMe_2SiOSiMe_3$; decamethyltetrasiloxane which has a boiling point of 194 degrees Centigrade and the formula $Me_3SiO(Me_2SiO)_2SiMe_3$; dodecamethylpentasiloxane which has a boiling point of 229 degrees Centigrade and the formula $Me_3SiO(Me_2SiO)_3SiMe_3$; tetradecamethylhexasiloxane which has a boiling point of 184 degrees Centigrade and the formula $Me_3SiO(Me_2SiO)_4SiMe_3$; and hexadecamethylheptasiloxane which has a boiling point of 184 degrees Centigrade and the formula $Me_3SiO(Me_2SiO)_5SiMe_3$.

Some representative cyclic volatile methyl siloxanes are hexamethylcyclotrisiloxane which has a boiling point of 133 degrees Centigrade and the formula $[(Me_2)SiO]_3$; octamethylcyclotetrasiloxane which has a boiling point of 171 degrees Centigrade and the formula $[(Me_2)SiO]_4$; decamethylcyclopentasiloxane which has a boiling point of 205 degrees Centigrade and the formula $[(Me_2)SiO]_5$; and dodecamethylcyclohexasiloxane which has a boiling point of 245 degrees Centigrade and the formula $[(Me_2)SiO]_6$.

Generally, the volatile methyl siloxanes may be used alone, or mixed together. Mixtures of the fluids will result in a volatile material having an evaporating behavior different from any one of the individual fluids.

A petition to the EPA filed in late 1992 is pending seeking exemption of these volatile methyl siloxanes (VMS) from regulation as a volatile organic compound (VOC). The basis for the petition is that the volatile methyl siloxanes do not contribute to, and in some cases actually inhibit the formation of tropospheric ozone. Thus, the volatile methyl siloxanes have a lower ozone formation potential than ethane, which is the most reactive compound on a list of "exempt" VOC.

Furthermore, these volatile methyl siloxanes (VMS) have an atmospheric lifetime of between 10 to 30 days. Consequently, VMS compounds do not contribute significantly to global warming. Volatile methyl siloxanes have no potential to deplete stratospheric ozone due to their short atmospheric lifetimes so that they will not rise and accumulate in the stratosphere. VMS compounds also contain no chlorine or bromine atoms.

Volatile methyl siloxane compounds (VMS) neither attack the ozone layer nor do they contribute to tropospheric ozone formation (Smog), and they have minimum GLOBAL WARMING potential. Volatile methyl siloxane compounds are hence unique in possessing these three attributes simultaneously.

These volatile methyl siloxanes provide a viable solution to the problem of finding a suitable replacement for "outlawed" chemicals heretofore commonly used as components in personal care products.

The procedure for making the clear, firm, gel according to the invention is simply a matter of combining and mixing together the three components. The mixture is heated to dissolve the gelator. The gel is formed when the mixture is cooled or allowed to cool.

The invention will be illustrated in more detail in the following examples. Three test methods were used in evaluating gels according to the invention. The gels were measured for their turbidity, penetration, and refractive index (RI).

For turbidity, gel samples were prepared in one-half ounce glass vials which fit into an Orbeco-Hellige Series 965 Digital Direct-Reading Turbidimeter. The gels were prepared and cast into the sample cells, allowed to set overnight, and measured on the turbidimeter by inserting the cell into the sample well and recording the reading. The measurements were recorded in Nephelometric Turbidity Units (NTU). These readings were all taken in the 000-999 NTU range which was calibrated daily.

For purposes of this invention, readings of less than 400 NTU are considered clear, readings greater than 400 NTU are considered translucent, and readings under 100 NTU are considered water clear.

For penetration, the same samples used in the turbidity measurements were measured for penetration, once the turbidity measurements had been recorded. The instrument used was a Precision Penetrometer fitted with a Humboldt H-1310 wax needle. The needle was lowered to the surface of the gel, the clutch was released for five seconds, and the readings were recorded in millimeters. Lower readings indicate hard gels, while higher readings indicate soft gels.

For Refractive Index (RI), the refractive indices were measured on a Bausch & Lomb Refractometer at twenty-one degrees Centigrade unless noted otherwise.

EXAMPLES 1 and 2

Examples 1 and 2 were conducted in one hundred gram batches by combining the ingredients shown below in a 250 milliliter beaker, stirring the ingredients, and heating the beaker contents to about 80°–85° Centigrade. When the mixtures were molten and clear, they were poured into containers. These two examples illustrate that the addition of an alkylmethylsiloxane hardens and clarifies the gel. This alkylmethylsiloxane is referred to hereinafter as "AMS #8", and it was prepared from a C30+alpha-olefin that had been reacted onto a siloxane polymer having an average degree of polymerization (DP) of twelve. The polymer contained 83 mole percent of the C30+alpha olefin.

| Ingredients | 1 | 2 |
|---|---|---|
| Octyl Methoxycinnamate | 18.6% | 10.0% |
| Octyl Salicylate | 4.7 | 5 |
| C12–15 Alcohol Benzoate | 71.1 | 79 |
| 12-hydroxystearic Acid | 5.6 | 5 |
| AMS #8 | 0 | 1 |
| Turbidity (NTU) | 690 | 250 |
| Penetration (mm) | 20 | 13 |

EXAMPLES 3 and 4

Examples 3 and 4 were conducted in the same manner as Examples 1 and 2. The refractive index (RI) of the blend of the first two siloxane ingredients was 1.5108 in each example.

| Ingredients | 3 | 4 |
|---|---|---|
| Diphenyltetramethyldisiloxane | 90.2% | 89.3% |
| Decamethylcyclopentasiloxane | 5.8 | 5.7 |
| 12-hydroxystearic Acid | 4 | 4 |
| AMS #8 | 0 | 1 |
| Turbidity (NTU) | 190 | 128 |
| Penetration (mm) | 28 | 23 |

EXAMPLES 5 and 6 —COMPARISON

Again, gel samples were prepared in the same manner as in Examples 1 and 2. The refractive index of the siloxane blend was 1.4970 in Examples 5 and 6. These examples illustrate that stearic acid does not function in the same manner as the alkylmethylsiloxanes of the invention. Thus, while stearic acid did harden the gel, unlike the alkylmethylsiloxane, it increased the turbidity of the gel.

| Ingredients | 5 | 6 |
|---|---|---|
| Tetraphenyltetramethyltrisiloxane | 60.0% | 59.4% |
| Decamethylcyclopentasiloxane | 36 | 35.6 |
| 12-hydroxystearic Acid | 4 | 4 |
| Stearic Acid | 0 | 1 |
| Turbidity (NTU) | 175 | >1000 |
| Penetration (mm) | 22 | 18 |

EXAMPLES 7–14

The following eight examples illustrate the use of several different alkylmethylsiloxanes (AMS #1 to AMS #8) in the preparation of gels. The gels were prepared in sixteen gram sizes by weighing the ingredients into one-half ounce vials using an analytical balance. The vials were capped and heated in a water bath to about 80°–85° Centigrade. The vials were shaken to ensure complete mixing. Once any air bubbles had been dissipated, the vials were placed in an ice bath and cooled. The siloxane compounds tetraphenyltetramethyl trisiloxane (TPTMTS) and decamethylcyclopentasiloxane (DMCPS), and the gelator 12-hydroxystearic acid (12-OH), are abbreviated below. Turbidity is shown in NTU units, and Penetration is in millimeters (mm). Example 7 was a CONTROL and contained no alkylmethylsiloxane.

| Ingredients | 7 | 8 | 9 | 10 | 11 | 12 | 13 | 14 |
|---|---|---|---|---|---|---|---|---|
| 12-OH | 3% | 3% | 3% | 3% | 3% | 3% | 3% | 3% |
| TPTMTS | 58.2 | 57.6 | 57.6 | 57.6 | 57.6 | 57.6 | 57.6 | 57.6 |
| DMCPS | 38.8 | 38.4 | 38.4 | 38.4 | 38.4 | 38.4 | 38.4 | 38.4 |
| AMS #1 | | 1 | | | | | | |
| AMS #2 | | | 1 | | | | | |
| AMS #3 | | | | 1 | | | | |
| AMS #4 | | | | | 1 | | | |
| AMS #5 | | | | | | 1 | | |
| AMS #6 | | | | | | | 1 | |
| AMS #7 | | | | | | | | 1 |
| Turbidity | 194 | 189 | 95 | 32 | 106 | 150 | 58 | 99 |
| Penetration | 32 | 32 | 26 | 24 | 25 | 32 | 25 | 22 |

EXAMPLE 15

The purpose of this example is to illustrate the preparation of an antiperspirant gel according to the invention. The first four ingredient shown below were added to a 150 milliliter Erlenmeyer flask as a 50 gram batch, and heated to 80° C. until dissolved. The mixture was de-aired using a vacuum pump. An encapsulated aluminum chlorohydrate prepared according to U.S. Pat. No. 5,320,828 was added to the flask and the contents were mixed. When the temperature of the flask was 60°–62° C., the contents were poured into an appropriate container.

| Ingredients | 15 |
|---|---|
| Tetraphenyltetramethyltrisiloxane | 54.8% |
| Decamethylcyclopentasiloxane | 20.2 |
| 12-hydroxystearic Acid | 4 |
| AMS #3 | 1 |
| Aluminum Chlorohydrate | 20 |
| Turbidity (NTU) | 75 |
| Penetration (mm) | 17 |

The alkylmethylsiloxanes AMS #1 to AMS #8 used in the examples are shown below. Siloxane A had the formula (Me)$_3$SiOMeHSiOSi (Me)$_3$; Siloxane B had the formula (Me)$_3$SiO[MeHSiO]$_6$[Me$_2$SiO]$_3$Si(Me)$_3$; and Siloxane C had the formula (Me)$_3$SiO[MeHSiO]$_{10}$Si(Me)$_3$ in which Me is methyl.

| ≡SiH Functional Siloxane Reacted | Olefins Reacted | | | | Alpha-Olefin Mole Percent |
|---|---|---|---|---|---|
| | C12 | C16 | C18 | C30 | |
| Siloxane A | | | AMS5 | AMS6 | 33.0 |
| Siloxane B | AMS1 | AMS2 | AMS3 | AMS4 | 55.0 |
| Siloxane C | | | AMS7 | AMS8 | 83 |

In the examples, it should be evident that the addition of a small amount of an alkylmethylsiloxane polymer or copolymer, to a gel containing 12-hydroxystearic acid and an organic oil or a siloxane fluid, improves the hardness and the clarity of the gel. In particular, gels prepared in accordance with Examples 9, 10, and 13–15, were "water clear" in that their turbidity readings were less than one hundred NTU as previously defined. Harder gels were obtained in Examples 2, 4, 9–11, and 13–15.

The benefit derived by the invention is that gels can now be formed by using reduced amounts of a gelator when the gelator is used in combination with an alkylmethylsiloxane. Heretofore, clarity was oftentimes sacrificed by employing high levels of gelator, but by including an alkylmethylsiloxane according to the invention, harder and clearer gels can now be obtained.

Other variations and modifications may be made in the compounds, compositions, and methods described without departing from the essential features and concepts of the invention. The forms of the invention described are exemplary only, and are not intended as limitations on the scope of the invention defined in the appended claims.

That which is claimed is:

1. A gel comprising an 0.1 to 10 percent by weight of an amide-free gelator selected from the group consisting of 12-hydroxystearic acid and metal salts of 12-hydroxystearic acid; 0.1 to 10 percent by weight of an alkylmethylsiloxane selected from the group consisting of:

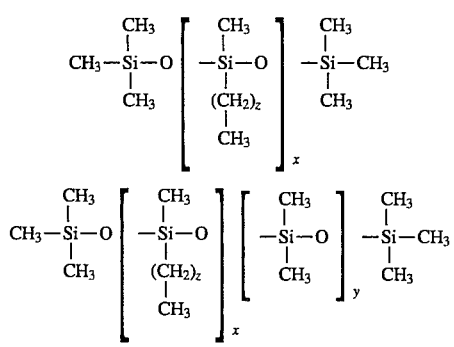

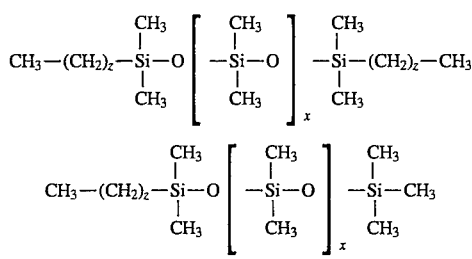

in which x has a value of 1–50; y has a value of 1–100; and z has a value of 10–40; 80 to 99.8 percent by weight of selected from the group consisting of:

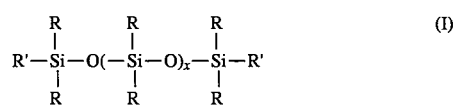

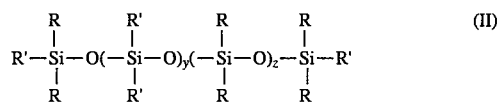

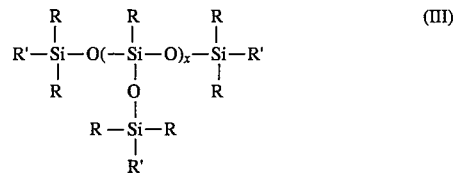

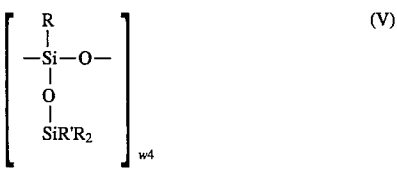

wherein R is selected from the group consisting of an alkyl radical with 1 to 7 carbon atoms, a phenyl radical, and an phenalkyl radical; R' is an alkyl radical of 1 to 7 carbon atoms; x has a value of zero to 1,000; w has a value of 3 to 6; y and z are each integers with a sum of 2 to 1,000; provided there are at least two phenyl groups as substituents on silicon atoms wherein the turbidity of the gel is less than 100 Nephelometiric Turbidity Units.

* * * * *

UNITED STATES PATENT AND TRADEMARK OFFICE
CERTIFICATE OF CORRECTION

PATENT NO. : 5,480,637

DATED : January 2, 1996

INVENTOR(S) : Janet Mary Smith

It is certified that error appears in the above-identified patent and that said Letters Patent is hereby corrected as shown below:

Column 12, line 16, should read "siloxane selected from the group consisting of:".

Signed and Sealed this

Twenty-sixth Day of March, 1996

Attest:

BRUCE LEHMAN

*Attesting Officer*  *Commissioner of Patents and Trademarks*